United States Patent [19]

Frank et al.

[11] Patent Number: 4,903,850
[45] Date of Patent: Feb. 27, 1990

[54] VAPORIZING DEVICE

[75] Inventors: Bernard Frank, 300 71st St., Suite 435, Miami Beach, Fla. 33141; Melvin B. Greenberg, North Miami Beach, Fla.

[73] Assignee: Bernard Frank, Miami Beach, Fla.

[21] Appl. No.: 323,464

[22] Filed: Mar. 14, 1989

[51] Int. Cl.$^4$ .......................... H05B 3/12; F22B 1/28
[52] U.S. Cl. .................................... 219/271; 219/275
[58] Field of Search ............... 219/271, 272, 273, 274, 219/275, 276, 436, 438, 362, 521

[56] References Cited

U.S. PATENT DOCUMENTS

| | | | |
|---|---|---|---|
| 1,930,038 | 10/1933 | Crowley | 219/271 |
| 1,998,327 | 4/1935 | McGuire | 219/272 |
| 3,139,885 | 7/1964 | Hirtz | 219/272 |
| 3,695,267 | 10/1972 | Hirtz | 219/272 |
| 3,949,743 | 4/1976 | Shanbrom | 219/272 |

*Primary Examiner*—Teresa J. Walberg
*Attorney, Agent, or Firm*—Caesar, Rivise, Bernstein, Cohen & Pokotilow, Ltd.

[57] ABSTRACT

A vaporizing device, preferably in the form of an inhaler, for directing steam in a downstream direction to the region of a user's face. A steam generating and control section includes a cup member for receiving a liquid to be vaporized, and a heater means is provided in a recess of the cup member for heating the liquid to generate steam. The generated steam is directed through a hood section attached to the steam generating and control section for directing the steam in a downstream direction to a user's face. The steam generating and control section includes at least one air-inlet slot for permitting ambient air to enter the device, an exit slot for permitting steam to exit the device, and an adjustable valve assembly downstream of the cup, air-inlet slot and exit slot to adjust the volume and velocity of steam flowing into the hood section. In a preferred form of the invention the heating of the liquid is controlled to cause vaporization only in a region adjacent raised walls defining a recess in the bottom wall of the cup member, and not in the region adjacent an outer peripheral wall of the cup member.

39 Claims, 4 Drawing Sheets

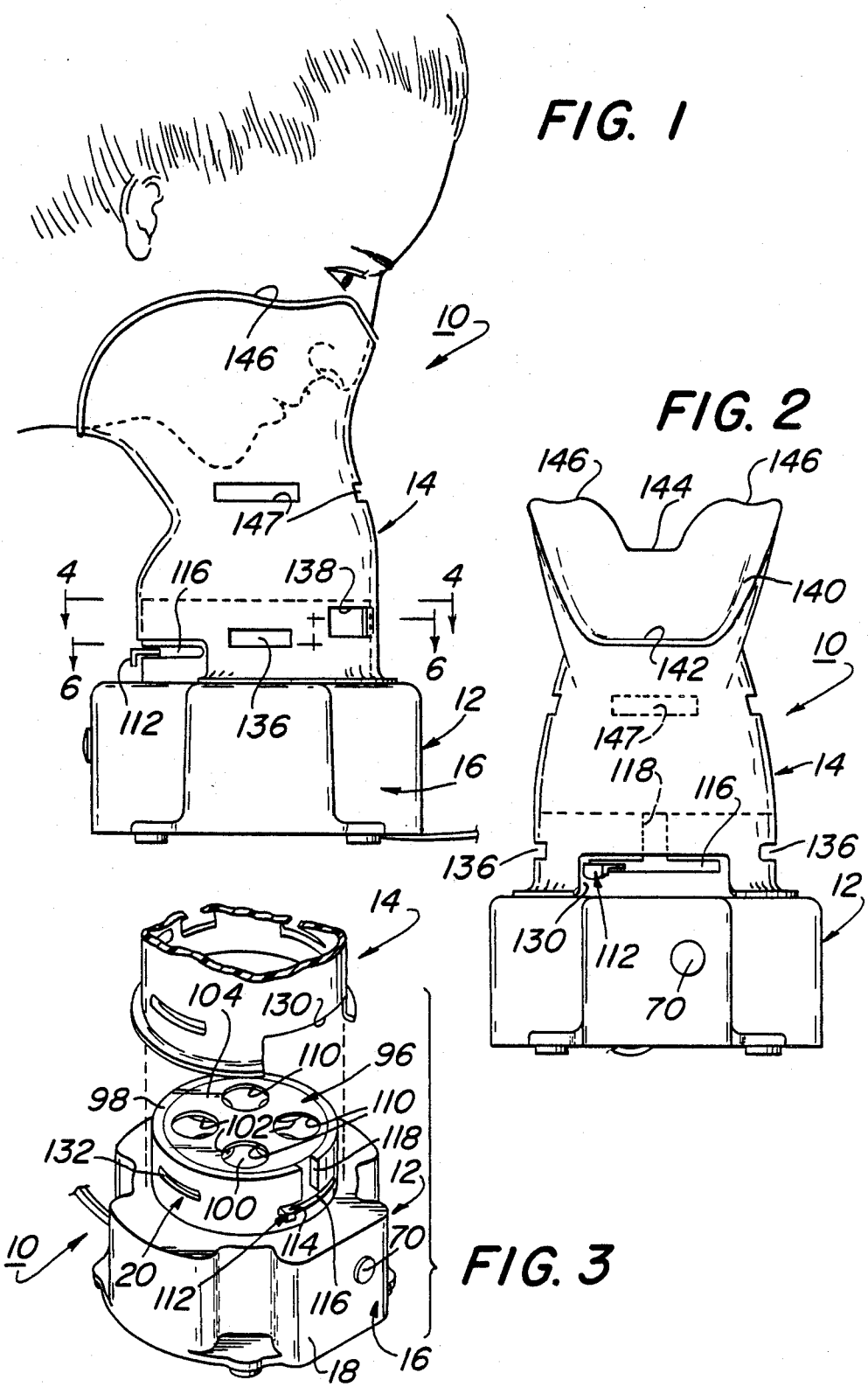

FIG. 8
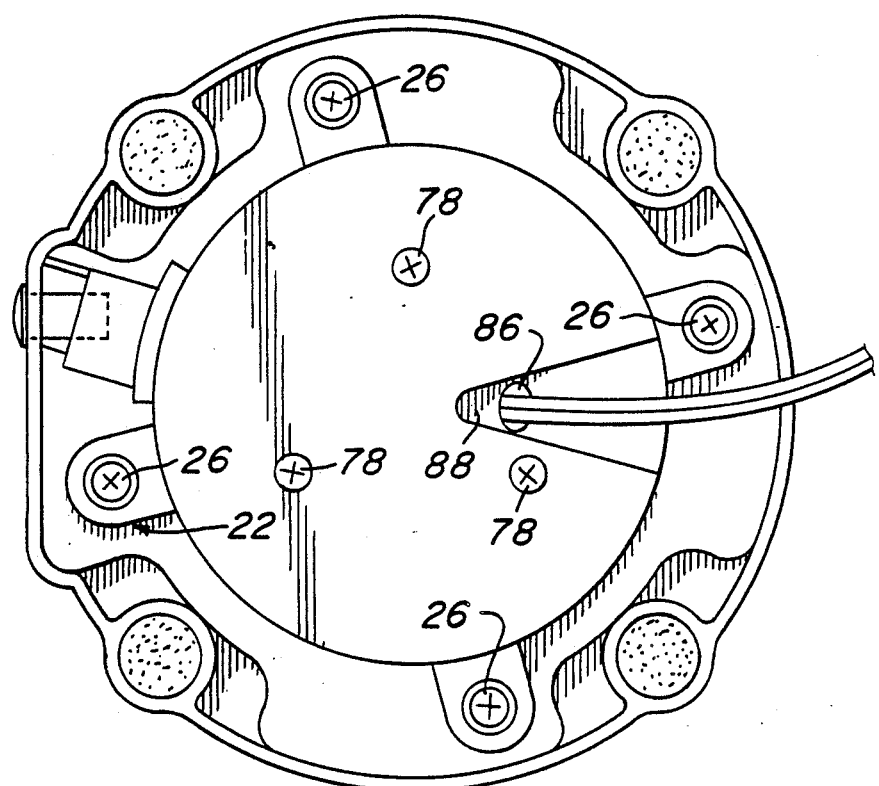
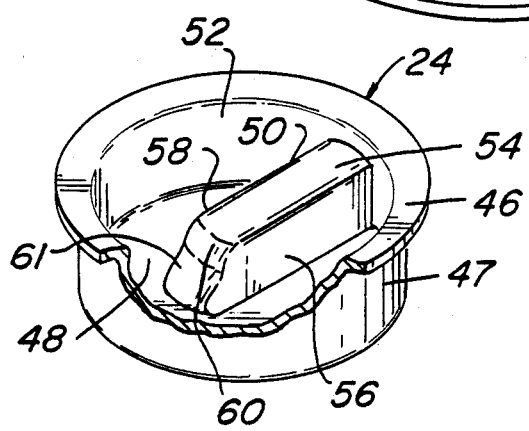
FIG. 9
FIG. 10
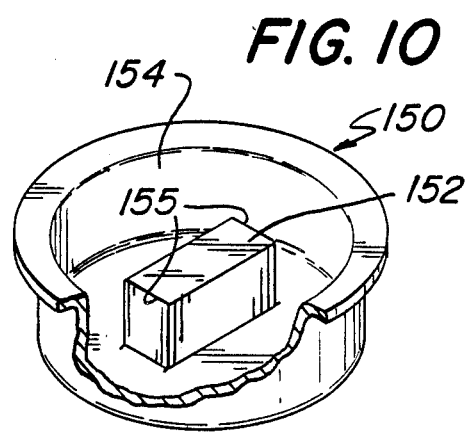

VAPORIZING DEVICE

FIELD OF THE INVENTION

This invention relates generally to a vaporizing device, and more specifically to a vaporizing device for directing steam to a user's face.

In the most preferred embodiment of the invention the vaporizing device is a lightweight inhaler unit for directing steam to the nose and mouth region of the user's face.

BACKGROUND ART

There are a variety of prior art vaporizing devices known in the prior art, and a number of these devices are employed to direct vapors, in the form of steam, to a user's face.

U.S. Pat. No. 4,700,050, issued to Hennuy et al., discloses a boiler arrangement for use in a variety of electrical appliances, including a facial sauna and an inhaler. In this device a positive temperature coefficient thermistor is employed as the heating element, and this heating element is retained within a recess formed in the bottom wall of a liquid retaining cup. In the Hennuy device the recess divides the cup into two separate compartments, and does not permit the flow of liquid between these compartments. In addition, the boiler and heater arrangement described in the paragraph beginning on line 58 of column 2 will create a vigorous boiling of the water, making it difficult to control the volume and velocity of steam flow to the user's face.

U.S. Pat. No. 3,351,737, issued to Katzman et al., discloses a facial treatment device employing a hood with cooling air-inlet slots provided at the base thereof to prevent the build-up of a vacuum within the hood, and also to partially cool the steam. This device does not employ a system for positively controlling the volume or velocity of steam flow to the user's face. Moreover, the provision of air-inlet slots in the hood, as disclosed in Katzman et al., will not effectively cool the steam directed to a user's face; particularly when the user's face is sealed against the upper margin of the hood.

U.S. Pat. No. 3,152,240, issued to Scott, discloses a vaporizing device which is intended to be employed for health and complexion care. However, this device, like the devices described in the above-identified patents to Hennuy et al. and Katzman et al., does not employ a system for positively controlling both the volume and velocity of steam flow to the user's face.

Bernard Frank, the inventor of the subject matter described and claimed herein, and Melvin B. Greenberg have jointly invented facial treatment devices, in the form of facial saunas, which are the subject of U.S. Pat. No. 4,621,641. Improvements to the facial sauna devices described in the Frank et al. '641 patent are the subject of pending patent application Ser. No. 053,285, filed on May 22, 1987, and entitled Vaporizer and/or Facial Treatment Device. In the devices described in the latter patent and pending application steam is generated in a casing member and then directed through a collapsible hood arrangement for providing facial treatment to a user's face. These latter devices, like the devices described earlier herein, do not include any system for positively controlling the volume, velocity and temperature of steam flow to a user's face. However, these devices have worked satisfactorily for their intended purpose; particularly because the user's face is not intended to be positioned in sealing engagement with the flowdirecting collapsible hood thereof.

In addition to the disclosure in the above-discussed Hennuy et al. '050 patent, the use of PTC electrical heating elements are disclosed in Steiner et al. U.S. Pat. No. 4,324,974, and in Kleinschmidt et al. U.S. Pat. No. 4,223,208. Other systems wherein a heating element is included in a recess of a device are disclosed in Mayall U.S. Pat. No. 1,381,322; Bernard U.S. Pat. No. 1,308,836; French No. 88,3862 and British Patent Specification No. 166,416. None of the devices disclosed in the patents identified in this paragraph include an arrangement for effectively controlling the volume and velocity of steam flow in an apparatus, such an inhaler, which is designed to direct the steam to a user's face.

OBJECTS OF THE INVENTION

It is a general object of this invention to provide a vaporizing device in the form of a lightweight appliance for directing steam to a user's face.

It is a more specific object of this invention to provide a vaporizing device in the form of a lightweight appliance for use as an inhaler, wherein the steam is directed only to the nose and mouth region of the user's face, while protecting the user's eyes from the exiting steam flow.

It is further object of this invention to provide a vaporizing device in the form of a lightweight appliance wherein the volume of steam flow directed to a user's face is positively controlled.

It is further object of this invention to provide a vaporizing device in the form of a lightweight appliance wherein the temperature of the steam directed to a user's face is effectively controlled in a simple, reliable and economical manner.

It is a further objection of this invention to provide a vaporizing device in the form of a lightweight appliance wherein the volume, velocity and temperature of steam flow to a user's face is effectively controlled.

SUMMARY OF THE INVENTION

The above and other objects of this invention are achieved in a vaporizing device for directing steam to a user's face, wherein the device includes a steam generating and control section and a hood section attached to the steam generating and control section for directing steam in a downstream direction to the user's face. The steam generating and control section includes a lower body section upstream of an upper body section, With the upper body section having a peripheral sidewall defining an interior passage. A cup member for receiving a liquid to be vaporized and a heater means for heating the liquid are retained in the lower body section. The upper body section includes slot means in the peripheral sidewall thereof for communicating the interior passage with ambient air, whereby cooling, ambient air effectively mixes with the steam to cool the steam as it is directed through a hood section to the region of a user's face.

In a preferred embodiment the hood section is attached to the steam generating and control section and extends in a downstream direction above the upper body section of said control section and terminates in an upper margin for receiving a user's face adjacent thereto. This upper margin also defines a steamflow confining passageway through which steam is directed to a region of the user's face aligned with the confining passageway.

In the most preferred embodiment of the invention the vaporizer device is an inhaler wherein the upper margin of the hood section is configured for surrounding the nose and mouth region of the user's face, while shielding the user's eyes from the flow of steam. Most preferably the upper margin of the hood section is configured to closely conform to the user's nose and cheek areas in a region below the user's eyes.

In a most preferred embodiment of this invention, wherein at least a portion of a user's face is adapted to be positioned in engagement with the upper margin of the hood, the hood section includes a first slot means in a lower section thereof which is aligned with slot means in the peripheral sidewall of the upper body section of the steam generating and control section, and a second slot means extending through a peripheral sidewall of an upper section of the hood section in a region downstream of the first slot means. In this manner extremely effective cooling of the steam is achieved, to thereby prevent discomfort to a user's face. This is extremely important for an inhaler of the type wherein the user's face actually is positioned in sealing engagement with the upper margin of the hood section.

In the most preferred embodiment of this invention the cup member for receiving the liquid (e.g., water) to be vaporized includes an upwardly directed recess in the bottom wall of the cup member for receiving and retaining a heating member therein, and an adjustable valve assembly is located downstream of the cup member for regulating the volume and velocity of steam flow exiting from the steam generating and control section.

Preferably the slot means in the steam generating and control section includes at least one air-inlet slot downstream of the cup member for permitting ambient air to enter the steam generating and control section and mix with steam moving in a downstream direction past the air-inlet slot, and at least one exit slot circumferentially offset from the air-inlet slot(s) and downstream of the air-inlet slot(s). This exit slot(s) permit(s) a portion of the steam generated in the device, either by itself or with a mixture of air from the air-inlet slot(s), to exit from the device, without impinging upon a user's face as the user is inhaling vapors from the device.

In accordance with another aspect of this invention the cup member has an outer peripheral wall and a bottom wall defining a compartment for the liquid to be vaporized. The bottom wall of the cup member is recessed upwardly to partially interrupt the compartment and to provide raised surfaces in contact with the liquid to be vaporized. A heater means, preferably in the form of a PTC thermistor, is retained within the recess for heating the raised surfaces to a temperature for vaporizing the liquid at the interface of the liquid with the raised surfaces, but not at the interface of the liquid with the outer peripheral wall, to thereby create a temperature gradient in the liquid from the raised surfaces provided by the recess to the outer peripheral wall of the cup. This arrangement for providing a temperature gradient, wherein boiling and vaporization of the water takes place only in a limited region adjacent the raised surfaces of the recess, aides in effectively controlling the temperature of the steam which is directed out of the device for impingement on a user's face.

In accordance with a preferred embodiment of this invention the adjustable valve assembly provides an opened passageway for the downstream flow of steam in all adjustable settings thereof. Thus, the device cannot be completely sealed off, to cause an undesired super heating of the steam therein.

In accordance with an additional feature of the invention the valve assembly includes a movable valve member, and the valve member has an actuating lever extending outwardly through a wall of the steam generating and control section for manual engagement by a user of the device. Most preferably the lever is in a front region of the device, the air-inlet slot(s) are provided in a side region(s) of the device and the exit slot is provided in a rear region of the device.

In the most preferred form of this invention two air-inlet slots are provided downstream of the cup member and upstream of a pair of exit slots. These air-inlet slots are located in side regions of the device, circumferentially offset from the exit slots, which are located at the rear of the device.

In a preferred embodiment of this invention the steam generating and control section includes a lower body section and an upper body section. The cup member for retaining the liquid to be vaporized and the heater means disposed in engagement with the cup member are located in the lower body section, and the air-inlet slot(s), the exit slot(s) and the adjustable valve assembly are associated with the upper body section. The junction between the upper body section and lower body section is provided by an upwardly facing shoulder, and the hood section is retained on the steam generating and control section by being received over the upper body section, with a lower surface of the hood section engaging the upwardly facing shoulder.

In the most preferred embodiment of the invention the section of the hood which is received over the upper body section of the steam generating and control section includes passageways through walls thereof in alignment with the air-inlet slot(s) and the exit slot(s).

BRIEF DESCRIPTION OF THE DRAWINGS

Other objects and many of the attendant advantages of this invention will be readily appreciated as the same becomes better understood by reference to the following detailed description when considered in connection with the accompanying drawings wherein:

FIG. 1 is a side elevational view of a vaporizing device in accordance with this invention, and showing the manner in which it is employed by a user, as an inhaler;

FIG. 2 is a front elevational view of the vaporizing device of FIG. 1;

FIG. 3 is an exploded, fragmentary view of the vaporizing device, showing certain details of construction;

FIG. 8 is a bottom view of the vaporizing device; and

FIG. 9 is an isometric view of a preferred cup member usable in the vaporizing device of this invention.

FIG. 10 is an isometric view of an alternative cup member usable in the vaporizing device of this invention.

DESCRIPTION OF THE PREFERRED EMBODIMENTS OF THE INVENTION

Figure 4:
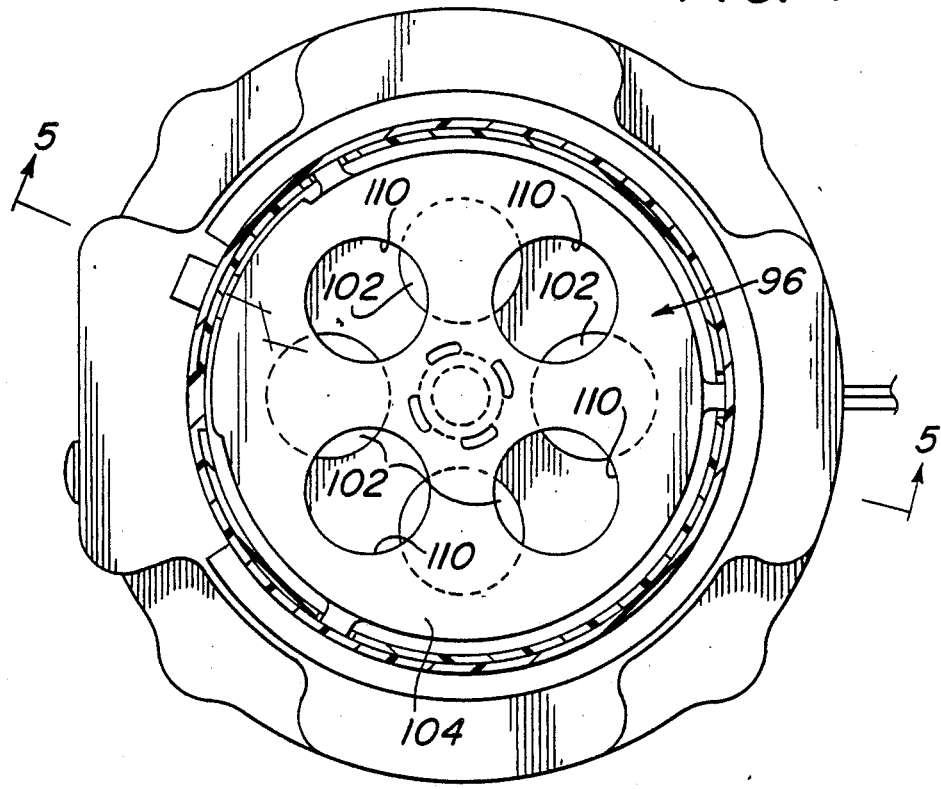
FIG. 4 is an enlarged sectional view taken along line 4—4 of FIG. 1.

Referring now in greater detail to the various figures of the drawings, wherein like reference characters refer to like parts, a vaporizing device embodying the present invention, in the form of an inhaler, is generally shown at 10 in FIG. 1. This device 10 basically comprises a steam generating and control section 12 in which a liquid, such as water, is heated to generate steam, and a hood section 14 for controlling the direction of steam flow to the area of a user's nose and mouth.

Figure 5:
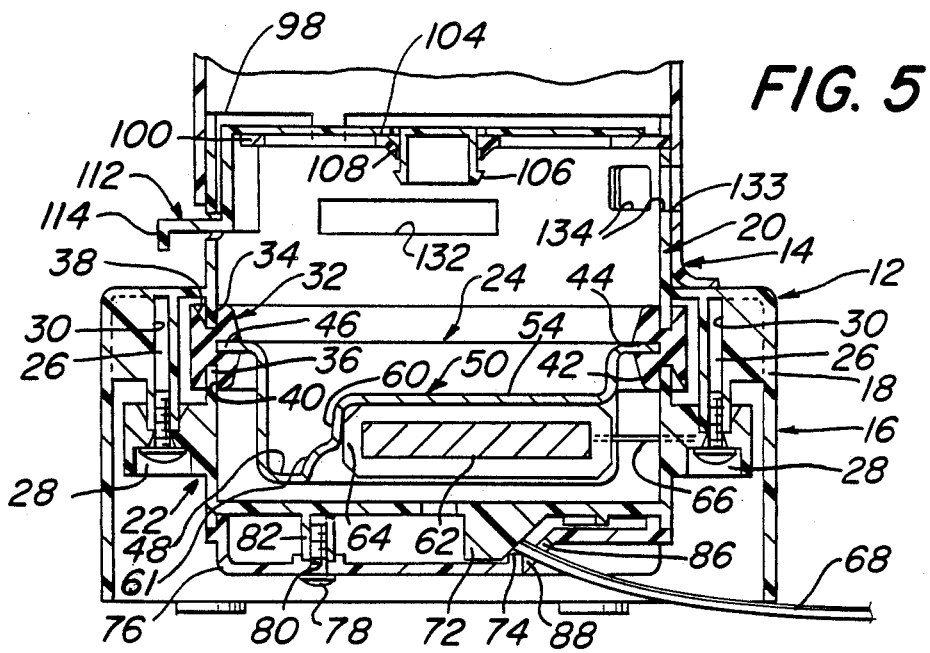
FIG. 5 is a sectional view taken along line 5—5 of FIG. 4.

Referring to FIGS. 3 and 5, the steam generating and control section 12 includes an outer plastic shell or housing 16 which preferably is molded as a single unit from a suitable plastics material, such as a polycarbonate. This housing includes a lower body section 18, in which the liquid is vaporized in a controlled manner for generating steam, and an upper body section 20, in the form of an annular hub, including means to be described in detail hereinafter for aiding in controlling the volume, velocity and temperature of steam flow out of the device.

Referring to FIGS. 5 and 8, the steam generating and control section 12 includes an inner liner 22 for partially enclosing a liquid-retaining (e.g., water-retaining) vessel or cup 24. This inner liner is removably secured in place by threaded screw members 26, each of which is received within aligned passages 28 and 30 in the liner 22 and housing 16, respectively.

Referring specifically to FIG. 5, an annular plastic gasket 32, preferably made of a suitable silicon material, is locked or clamped between a downwardly directed annular flange 34 forming part of the housing 16, and an upwardly directed annular flange 36 forming part of the inner liner 22. Cooperating recesses 38 and 40 in the gasket 32 receive the annular flanges 34 and 36, respectively.

Still referring to FIG. 5, the gasket 32 has an inner wall 42 provided with an annular slot 44. This annular slot receives the outwardly extending annular flange 46 of the cup 24, to thereby secure the cup in proper position within the vaporizing device 10.

Figure 6:
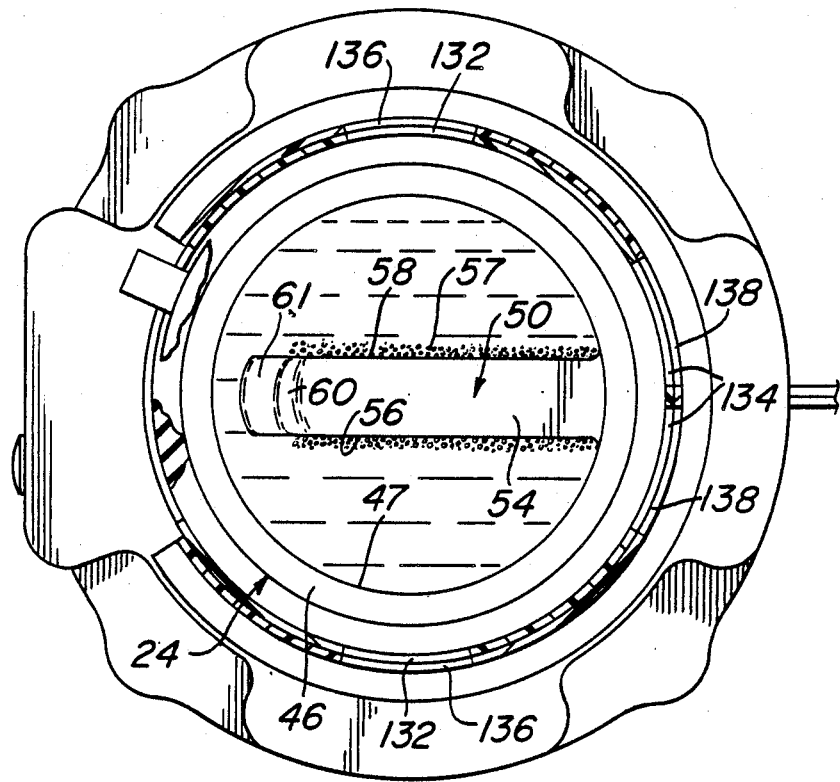
FIG. 6 is an enlarged sectional view taken along line 6—6 of FIG. 1.

Referring to FIGS. 5, 6 and 9, the vessel or cup 24 preferably is made of aluminum, and includes an outer peripheral wall 47 and a bottom wall 48. The bottom wall has an upwardly raised section 50 extending inwardly from the outer peripheral wall 47, but only partially across the width of the cup to thereby form a single, continuous compartment 52 in which the liquid to be vaporized is retained.

Still referring to FIGS. 5, 6 and 9, the upwardly raised section 50 includes a top wall 54, disposed inwardly of the upper margin of the cup, a pair of long, substantially planar sidewalls 56 and 58, which preferably are parallel to each other, and a short end wall 60. The end wall 60, in the preferred embodiment of the invention, is formed in a stepped configuration, with a lower portion 61 thereof being formed as a portion of a sphere to thereby prevent the build-up of excessive stresses which can cause the cup 24 to fracture in regions of the raised section 50. However, depending upon the hardness of the material employed to form the cup 24, it may be possible to eliminate the stepped configuration of the end wall 60 without creating a stress fracture problem. A heating element 62, preferably in the form of a positive temperature coefficient (PTC) thermistor, is frictionally secured within recess 64, which is defined within the upwardly raised section 50. If desired the PTC heater can be bonded to inner surfaces defining the recess 64, with a heat conductive bonding agent; however, the use of a bonding agent is not believed to be necessary.

Figure 7:
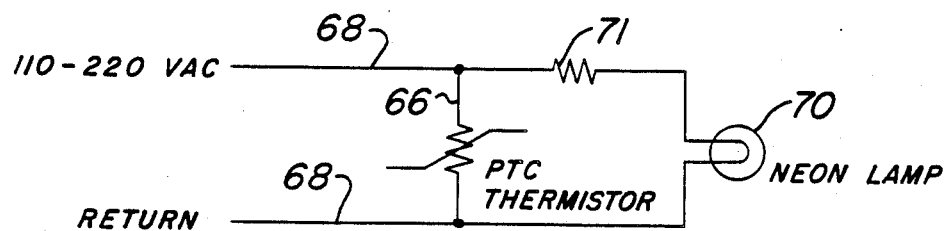
FIG. 7 shows a schematic circuit arrangement for the heater and on/off indicator lamp of the vaporizing device.

Referring to FIGS. 5 and 7, the PTC heater is connected through a suitable lead 66 to a conventional insulated conductive wire 68 having a plug (not shown) at one end thereof for connection to a conventional household electrical outlet; either 110 VAC or 220 VAC.

Referring to FIGS. 2 and 7, a light source, preferably in the form of a neon lamp 70, is connected to the current source through a current-limiting resistor 71, in parallel with the PTC heater, to thereby light up when the vaporizing device 10 is "on" (i.e., when the device is plugged in). If desired a switch (not shown) can be provided in the circuit to turn the device on and off.

Referring to FIGS. 5 and 8, the conductive wire 68 extends through a passage provided in a downwardly extending projection 72 forming part of lower wall 74 of the inner liner 22. In addition, much of the wiring (not shown) is secured by suitable clip members below the lower wall 74, and is enclosed by a lower plate member 76. Threaded screws 78 are each received within aligned passages 80, 82 of the lower plate member 76 and lower wall 74, respectively, of the inner liner 22, to thereby threadedly secure the lower plate member to the inner liner 22. As can be seen best in FIG. 5, the lower wall of the plate member 76, in a region adjacent the conductive wire 68, is provided with an upwardly extending tab 84 for pushing the wire into slot 86, which is formed by an inwardly directed section 88 of bottom wall 90 of said plate member.

In a preferred embodiment of this invention an adjustable valve assembly 96 is located adjacent outer marginal edge 98 of the hub 20, for aiding in controlling the volume and velocity of steam flow which is directed from the vaporizing device 10 to a user's face. It also is within the scope of this invention to employ a variable heater to control the intensity (i.e., velocity and volume) of steam generated in the device 10.

Referring specifically to FIGS. 2 through 5, the adjustable valve assembly 96 includes a stationary grill 100 having a plurality of openings 102 provided therethrough. These openings are circumferentially spaced apart an equal distance from each other, as can be seen best in FIG. 4.

An adjustable valve plate 104 includes a central hub 106 which is rotatably received within a central passage 108 of a stationary grill 100. This valve plate includes a plurality of openings 110 which, like the openings 102 in the stationary grill 100, are circumferentially spaced apart an equal distance from each other. An actuating lever 112 forms a part of the adjustable valve plate 104, and includes a horizontal arm 114 extending outwardly through an arcuate, horizontal passage 116 provided in the upper section 20 of the housing 16. As can be seen best in FIGS. 2 and 3, a vertical slot 118 extends from outer marginal edge 98 of the upper body section 20 to the arcuate passage 116, to thereby permit the adjustable valve plate 104 to be easily positioned on, and removed from the stationary grill 100.

As can be seen best in FIG. 3, the relative spacing between the openings 110 in the adjustable valve plate 104, on the one hand, and the openings 102 in the stationary grill 100, on the other hand, precludes the complete "closing off" or "sealing" of the openings 102.

FIG. 3 clearly shows that a portion of the openings 102 remains open for the passage of steam therethrough, even when the lever is at the extreme end of the arcuate passage 116. This arrangement assists in preventing the excessive pressure build-up of steam within the confines of the steam generating and control section 12, to thereby aid in preventing the undesired super heating of the steam. If the steam is super heated it can scald or otherwise injure the user's face.

Referring to FIGS. 2 and 3, the lower end of the hood section 14, which is received over the annular hub 20, includes a recess 130 aligned with both the arcuate passage 116 and the lever 112 extending therethrough. This arrangement prevents the hood from interfering with the desired transverse movement of the lever 112 for controlling the volume and velocity of steam directed out of the device 10. It should be noted that the lever 112 preferably is positioned adjacent the front of the device, along with the neon lamp 70.

Referring to FIGS. 1, 3, 5 and 6, the upper, annular section 20 of the housing 16 includes an elongate air-inlet slot 132 adjacent each side of the device 10, and a pair of elongate exit slots 134 adjacent the rear of the device. Both air-inlet slots preferably are of the same dimension and are in the same transverse plane. The exit slots 134 preferably have at least a segment thereof located downstream (in the direction of steam flow) of the air-inlet slots 132 and closely adjacent to the underside of the stationary grill 100 of the adjustable valve assembly 96. For ease of molding an upper or downstream segment of each air-inlet slot 132 is in transverse alignment with a lower or upstream segment of exit slot 134. However, from the standpoint of functionality, the important feature is that at least a segment of the exit slot is downstream of the air-inlet slots.

The lower region of the hood section 14, which is positioned over the annular hub 20, includes elongate slots 136 for aligning with the air-inlet slots 132, and slots 138 for aligning with the exit slots 134 (FIG. 6). For ease of molding, and as can be seen best in FIG. 1, the elongate slot 138 has a segment located downstream of the elongate slots 136, and a segment in transverse alignment with a portion of the elongate slots 136. This arrangement of aligned slots in the hub 20 and hood 14 provides a through-passageway for ambient air flow into the hub 20 through the air-inlet slots 136 and 132, and for steam flow out of the device through the exit slots 134 and 138 when a person is inhaling vapors through hood section 14.

Referring specifically to FIGS. 1 and 2, the hood section 14 has an upper margin 140 including a recessed region 142 adjacent the front of the device, for receiving and/or supporting a portion of the user's jaw/neck. The rear portion of the upper margin includes a recessed section 144 for closely sealing against the bridge of the user's nose, as can be seen best in FIG. 1. Segments 146 adjacent the recessed section 144 extend below the eyes for sealing against the user's cheekbones. As a result of this arrangement the steam directed through the hood section 114 impinges upon the user's nose and mouth, without unduly irritating his or her eyes. To further control the steam temperature impinging upon the user's face the hood is provided with three circumferentially spaced apart air-inlet passages 147 located in a region downstream of the hub 20 (FIG. 1). This permits additional, cooling, ambient air to mix with the steam just prior to impingement on the user's face, as the user is inhaling vapors.

It should be understood that the slots 132 in the hub 20 and the passages 147 in the hood 14 function to permit ambient air to flow into the confines of the unit when a user of the device has his or her face positioned in engagement with the upper margin 140 of the hood, as shown in FIG. 1, and is inhaling vapors. It is during this same mode of operation that the slots 134 adjacent the rear of the device permit steam (and air mixed therewith) to exit from the hub without engaging the user's face. When a person exhales with his or her face adjacent the upper margin 140 of the hood it is entirely possible that all of the above-discussed slots and passages (i.e., 132, 134 and 147) will function to permit the escape of steam and air, to thereby relieve the internal pressure created by exhaling.

Unless specifically stated otherwise all references in this application to slots or passages functioning as inlet or exit slots describes the function achieved when a person is inhaling vapors through the upper margin 140 of the hood 14.

Referring specifically to FIG. 6, another very important feature of this invention resides in a unique arrangement for heating and vaporizing the liquid in the cup 24, to avoid generating an excess volume of steam. In fact, in accordance with this invention the steam generating system permits the generation of just the right amount of steam, without requiring the use of a separate thermostat.

Referring specifically to FIG. 6, the liquid to be vaporized is equally distributed within the single compartment 52 so as to engage the opposed upstanding planar sidewalls 56, 58 of the upwardly raised section 50. The PTC heater 62 is retained within the recess 64 and directs heat through the planar sidewalls 56, 58, for the purpose for heating the liquid within the compartment 52 to generate steam. In accordance with this invention the PTC heater 62 and the cup 24 are selected to control the temperature of the water in the compartment 52 so that only the portion of the water located close to the planar sidewalls 56 and 58 of the raised section 50 will boil (i.e., vaporize), as is schematically illustrated at 57 in FIG. 6, with the portion of the water adjacent the outer peripheral wall of the cup 24 being at a temperature below the boiling point. In the most preferred embodiment of this invention the boiling of the water takes place substantially only at the interface of the water with the elongate planar sidewalls 56, 58 of the raised section 50, and the temperature adjacent the outer periphery of the water-retaining vessel is at approximately 92° C. (197° F.). Providing such a temperature gradient, wherein boiling takes place only adjacent the planar sidewalls 56,58 of the raised section 50, provides extremely effective control over the volume of steam which is generated within the device, and thereby aids in preventing the super heating of the steam.

As discussed above, the upper body section 20 includes an exit slot 134 adjacent the rear of the device and also closely adjacent to the adjustable valve assembly 96. This exit slot permits a portion of the steam generated within the unit to exit from the device 10, without impinging upon the user's face. This arrangement assists in preventing an excessive build-up of steam pressure, which can have the adverse effect of super heating the steam which is impinged upon the user's face.

Applicant has discovered that in order to permit the steam to exit from the slot 134 it is necessary to equalize the pressure under the stationary grill 100 of the adjustable valve assembly 96. In accordance with this invention the pressure under the grill 100 is equalized by the provision of the aforementioned air-inlet slots 132 located adjacent the sides of the device 10, upstream of the exit slot 134. This arrangement of air-inlet and exit slots channels the air/steam flow such that ambient air enters the inlet slots, mixes with the steam, and is directed toward the exit slot at the rear of the device, since this is the path of least resistance for the flow of the steam and incoming air. This arrangement permits a desired quantity of steam to exit from the device, below the grill, to thereby reduce the internal pressure for preventing the super heating of the steam within the fixed volume under the adjustable valve assembly 96. It is most preferred to include the air-inlet slots 132 below (i.e., upstream) at least a downstream portion of the exit slot 134 to prevent the creation of turbulent flow. Moreover, ambient air will tend to enter the lower slots, whereas the steam which is generated tends to exit from the upper exit slot adjacent the lower surface of the adjustable valve assembly 96.

In an exemplary embodiment of the invention the liquid-retaining cup 24 is made from aluminum sheet stock having a thickness of approximately 80 mils. The cup is formed to have a height of approximately ¾ of an inch and an outside diameter of approximately 2.67 inches. The recess 64 provided by the pierlike raised section 50 has an elongate dimension of approximately 2 inches, a narrow transverse dimension of approximately 0.277 inches and a height of approximately 0.57 inches. This arrangement defines a single liquid-retaining compartment 52 which is capable of retaining up to about 40 cc (1.35 ounces) of water therein without overflowing the raised section 50. The PTC heater has a power output during boiling of less than 100 watts, and preferably less than 50 watts. In the most preferred embodiment the power output during boiling is approximately 47 watts, and functions to cause the water to boil substantially only at the interface between the water and the long surfaces of the raised section 50. The temperature of the water adjacent the outer peripheral wall 47 thereof is below its boiling point, and preferably is less than 200° F. Therefore no steam is generated adjacent the outer peripheral wall of the cup 24.

When the water fully evaporates (e.g., in about 30 minutes) the PTC heater heats the cup to a maximum temperature in the range of 300°-350 degrees F., and then the heater automatically regulates itself to maintain this temperature, as if it were thermostatically controlled (but without actually using a thermostat).

Since the PTC heater is linear in the region of application, its behavior at 220 VAC is virtually the same as at 110 VAC applied. Thus, the PTC heater employed in this invention provides an automatic means of heating with either voltage.

An alternative liquid-retaining cup usable in the device 10 of this invention is generally shown at 150 in FIG. 10. This cup has substantially the same dimensions as the cup 24, but like the cup 24, is made from aluminum or other suitable heat-conductive material. The only difference between the cup 150 and the cup 24 is in the arrangement and dimensions of the upwardly raised section which provides the recess for receiving the heating element 62. In the cup 24 the upwardly raised section 50 extends inwardly from peripheral outer wall 47, in a "fishing pier" arrangement. In the cup 150 the upwardly raised section 152 is in the form of an "island." Moreover, the elongate dimension of the raised section 152 is less than the elongate dimension of the raised section 50. Since the elongate dimension of the raised section 152 is less than the elongate dimension of the raised section 50, it is not believed necessary to form the end walls 155 of a stepped configuration in order to avoid the earlier-discussed stress fracturing problem. However, the cup 150, like the cup 24, includes a single, continuous compartment 154 for receiving the liquid to be vaporized therein. Thus, when the liquid to be vaporized is introduced into the cup 150 it will equalize in volume throughout the compartment 154.

From the above discussion it should be noted that the vaporizing device 10 of this invention includes a unique combination of elements for achieving desired control of the volume, velocity and temperature of the steam generated therein. The design of this invention gives the benefit of a long inhalation in low or high steam. If desired, an additive with soothing properties can be added to the liquid (e.g., water) in the cup to possibly enhance the effectiveness of the inhalation.

Without further elaboration the foregoing will so fully illustrate my invention that others may, by applying current or future knowledge, adopt the same for use under various conditions of service.

What we claim as the invention is:

1. A vaporizing device for directing steam in a downstream direction to the region of a user's face, said device including:
   (a) a steam generating and control section including a lower body section upstream of an upper body section, said upper body section having a peripheral sidewall defining an interior passage, a cup member for receiving a liquid to be vaporized and a heater means for heating said liquid being retained in said lower body section, said upper body section including slot means in the peripheral sidewall thereof and an adjustable valve assembly downstream of the cup member and the slot means for regulating the volume and velocity of steam flow exiting from said steam generating and control section;
   (b) a hood section having an upstream end attached to said steam generating and control section and including slot means aligned with the slot means in the peripheral sidewall of the upper body section of the steam generating and control section for communicating the interior passage of the upper body section with ambient air, said hood section extending in a downstream direction above the upper body section and terminating in an upper margin, said upper margin receiving a user's face adjacent thereto and defining a steam-flow confining passageway for directing steam to a region of the user's face aligned with said confining passageway.

2. The vaporizing device of claim 1 characterized in that the upper margin of the hood section is configured for surrounding the nose and mouth region of a user's face while shielding the user'eyes from the flow of steam.

3. The vaporizing device of claim 2 characterized in that the upper margin of the hood section is configured to closely conform to the user's nose and cheek areas in a region below the user's eyes.

4. The vaporizing device of claim 1 characterized in that said slot means in the peripheral sidewall of the upper body section of the steam generating and control section includes an air-inlet slot downstream of said cup member for permitting ambient air to enter the steam generating and control section and mix with steam moving in a downstream direction passed said air-inlet slot, and an exit slot for a portion of the steam and air mixture spaced downstream from the air-inlet slot, said exit slot being adjacent to and upstream of said valve assembly and circumferentially offset from the air inlet slot.

5. The vaporizing device of claim 4 characterized in that the adjustable valve assembly provides an open passageway for the downstream flow of steam in all adjustable settings of said assembly.

6. The vaporizing device of claim 4 characterized in that the upper margin of the hood section is configured to closely conform to the user's nose and cheek areas in a region below the user's eyes.

7. A vaporizing device for directing steam in a downstream direction to the region of the user's face, said device including a steam generating and control section including a lower body section upstream of an upper body section, said upper body section having a peripheral sidewall defining an interior passage, a cup member for receiving a liquid to be vaporized and a heater means for heating said liquid being retained in said lower body section, said upper body section including slot means in the peripheral sidewall thereof; and a hood section including a lower section surrounding the upper body section of the steam generating and control section and an upper section extending in a downstream direction from said lower section, said upper section terminating in an upper margin, said upper margin receiving a user's face adjacent thereto, said lower section having first slot means therein aligned with the slot means in the peripheral sidewall of the upper body section of the steam generating and control section for communicating the interior passage of the upper body section with ambient air, and second slot means extending through a peripheral sidewall of the upper section of the hood section in a region downstream of said first slot means.

8. The vaporizing device of claim 7 characterized in that the upper margin of the hood section is configured to closely conform to the user's nose and cheek areas in a region below the user's eyes.

9. A vaporizing device for directing steam in a downstream direction to the region of a user's face, said device including:
(a) a steam generating and control section having a cup member for receiving a liquid to be vaporized therein; a recess in the bottom wall of said cup member for retaining a heater means therein; a heater means retained in said recess; an adjustable valve assembly downstream of the cup member for regulating the volume and velocity of steam flow exiting from said steam generating and control section; an air-inlet slot downstream of said cup member for permitting ambient air to enter the steam generating and control section and mix with steam moving in a downstream direction passed said air-inlet slot; and an exit slot for a portion of the steam and air mixture spaced downstream from the air-inlet slot, adjacent to and upstream of said valve assembly and circumferentially offset from the air inlet slot; and
(b) a hood section attached to said steam generating and control section for directing steam that passes through the adjustable valve assembly in a downstream direction to a user's face.

10. The vaporizing device of claim 9 characterized in that the adjustable valve assembly provides an open passageway for the downstream flow of steam in all adjustable settings of said assembly.

11. The vaporizing device of claim 9 characterized in that said valve assembly includes a movable valve member, said valve member having an actuating lever means extending outwardly through a wall of the steam generating and control section for manual engagement by a user of the device, said air-inlet slot being circumferentially offset from the lever means.

12. The vaporizing device of claim 9 characterized in that a pair of air-inlet slots are provided downstream of said cup member and upstream of said exit slot, said pair of air-inlet slots both being circumferentially offset from said exit slot.

13. The vaporizing device of claim 9 characterized in that a pair of air-inlet slots are provided downstream of said cup member and upstream of said exit slot, said valve assembly including a movable valve member, said valve member having an actuating lever means extending outwardly through a wall of the steam generating and control section for manual engagement by a user of the device, said pair of air-inlet slots both being circumferentially offset from said lever means and from said exit slot.

14. The vaporizing device of claim 13 characterized in that said lever means is located in a front region of the device, said air-inlet slots are located in side regions of the device and said exit slot is located in a rear region of the device.

15. The vaporizing device of claim 9 characterized in that said steam generating and control section includes a lower body section and an upper body section, said cup member and heater means being disposed in said lower body section and said air-inlet slot, said exit slot and said adjustable valve assembly being associated with the upper body section, the junction between said upper body section and said lower body section providing an upwardly facing shoulder, said hood section being retained on said steam generating and control section by being received over said upper body section with a lower surface of said hood section engaging said upwardly facing shoulder.

16. The vaporizing device of claim 9 characterized in that the section of said hood which is received over said upper body section includes passages through walls thereof in alignment with the air-inlet slot and the exit slot.

17. A vaporizing device for directing steam in a downstream direction to the region of a user's face, said device including:
a) a steam generating and control section having a cup member, said cup member having an outer peripheral wall and a bottom wall defining a compartment for receiving therein a liquid to be vaporized, the bottom wall of said cup member being recessed upwardly to partially interrupt the compartment and to provide raised surfaces in contact with said liquid; a heater means retained in said recess for heating said raised surfaces to a temperature for vaporizing liquid at the interface of the liquid with the raised surfaces, but not at the interface of the liquid with the outer peripheral wall, to thereby create a temperature gradient in the liquid from the raised surfaces provided by the recess to the outer peripheral wall, for aiding in effectively controlling the volume and temperature of steam directed out of said steam generating and control section;

(b) an adjustable valve assembly provided adjacent a downstream end of the steam generating and control section for aiding in regulating the volume and velocity of steam flow exiting therefrom; an air-inlet slot downstream of said cup member and upstream of said adjustable valve assembly for permitting ambient air to enter the steam generating and control section and mix with steam moving in a downstream direction passed said air-inlet slot, and an exit slot for a portion of the steam, said exit slot being spaced downstream from the air-inlet slot, adjacent to and upstream of said valve assembly and circumferentially offset from the air inlet slot; and (c) a hood section attached to said steam generating and control section for directing steam in a downstream direction to a user's face.

18. The vaporizing device of claim 17 characterized in that the heater means is a positive temperature coefficient (PTC) thermistor.

19. The vaporizing device of claim 17 characterized in that the adjustable valve assembly provides an open passageway for the downstream flow of steam in all adjustable settings of said assembly.

20. The vaporizing device of claim 17 characterized in that said valve assembly includes a movable valve member, said valve member having an actuating lever means extending outwardly through a wall of the steam generating and control section for manual engagement by a user of the device, said air-inlet slot being circumferentially offset from the lever means.

21. The vaporizing device of claim 17 characterized in that a pair of air-inlet slots are provided downstream of said cup member and upstream of said exit slot, said pair of air-inlet slots both being circumferentially offset from said exit slot.

22. The vaporizing device of claim 17 characterized in that said steam generating and control section includes a lower body section and an upper body section, said cup member and heater means being disposed in said lower body section and said air-inlet slot, said exit slot and said adjustable valve assembly being associated with the upper body section, the junction between said upper body section and said lower body section providing an upwardly facing shoulder, said hood section being retained on said steam generating and control section by being received over said upper body section with a lower surface of said hood section engaging said upwardly facing shoulder.

23. The vaporizing device of claim 17 characterized in that the section of said hood which is received over said upper body section includes passages through walls thereof in alignment with the air-inlet slot and the exit slot.

24. The vaporizing device of claim 17 characterized in that a pair of air-inlet slots are provided downstream of said cup member and upstream of said exit slot, said valve assembly including a movable valve member, said valve member having an actuating lever means extending outwardly through a wall of the steam generating and control section for manual engagement by a user of the device, said pair of air-inlet slots both being circumferentially offset from said lever means and from said exit slot.

25. The vaporizing device of claim 17 characterized in that said lever means is located in a front region of the device, said air-inlet slots are located in side regions of the device and said exit slot is located in a rear region of the device.

26. A method of controlling the volume of steam generated in a vaporizing device of the type employed for directing the steam in a downstream direction to the region of a user's face, said device including a steam generating and control section including a cup member having an outer peripheral wall and a bottom wall defining a compartment for receiving therein a liquid to be vaporized, the bottom wall of said cup member being recessed upwardly to partially interrupt the compartment and provide raised surfaces in contact with said liquid, and a heater means retained in the recess of the bottom wall, said method including the steps of:

(a) introducing a liquid to be vaporized into the compartment of the cup member;

(b) choosing a heater means in relation to the liquid to be vaporized and the size and material of the cup member, such that said heater means can be energized to boil the liquid only in a region adjacent the raised surfaces and not in a region adjacent the outer peripheral wall of the cup member; and (c) energizing the heater means in a manner for boiling the liquid only in a region adjacent the raised surfaces and not in a region adjacent the outer peripheral wall of the cup member.

27. The method of claim 26 wherein the step of energizing the heating means is carried out to boil said liquid substantially only at the interface of the liquid with the raised surfaces, thereby creating a temperature gradient in the liquid from a region adjacent the raised surfaces to the outer peripheral wall of the cup member.

28. The method of claim 27 including the step of maintaining the power output of the heater means at less than 100 watts during boiling of the liquid.

29. The method of claim 26 wherein said liquid is water, and wherein the step of energizing the heating means is carried out to maintain the temperature of the water adjacent the outer peripheral wall at less than 200° F., and the temperature of the water adjacent the raised surfaces at substantially 212° F.

30. The method of claim 26 including the step of maintaining the power output of the heater means at less than 100 watts during boiling of the liquid.

31. A hood for a vaporizing device of the type for directing steam from a steam generating section of the device to a region of a user's face, characterized in that said hood includes an upstream end adapted to be attached to the steam generating section and a downstream end terminating in an upper margin, said upper margin adapted to receive a user's face adjacent thereto and defining a steam-flow confining passageway through which steam passes to a region of a user's face aligned with said passageway, first slot means extending through a peripheral wall of said hood for communicating the hood with ambient air and second slot means extending through a peripheral wall of said hood downstream from said first slot means for communicating said hood with ambient air, said first slot means being adapted to align with slot means in a peripheral sidewall of the steam generating section, and said second slot means being disposed in a location which is downstream of said steam generating section when the hood is attached to the steam generating section.

32. The hood of claim 31 characterized in that the upper margin thereof is configured for surrounding the nose and mouth region of a user's face while shielding the user's eyes from the flow of steam therethrough.

33. The hood of claim 32 characterized in that the upper margin is configured to closely conform to the user's nose and cheek regions in a region below the user's eyes.

34. A vaporizing device for generating steam and directing said steam in a downstream direction to the region of a user's face, said device including:
(a) a cup member for receiving a liquid to be vaporized;
(b) a heater means for heating liquid in said cup member for generating steam;
(c) a hood section for receiving steam generated by the heating of the liquid in the cup member, said hood section including an upper margin at a downstream end thereof, said upper margin receiving a user's face adjacent thereto and defining a steam-flow confining passageway for directing steam to a region of the user's face aligned with said confining passageway; and
(d) an adjustable valve assembly disposed downstream of the cup member and upstream of the upper margin of the hood section, for regulating the volume and velocity of steam flow directed through the upper margin of the hood section, said adjustable valve assembly providing an open passageway for the downstream flow of steam from the cup member, in all adjustable settings of said assembly.

35. The vaporizing device of claim 34 characterized in that the cup member, the heater means and the adjustable valve assembly are all disposed in a lower steam generating and control section, said hood section being attached to said steam generating and control section for channeling the flow of steam to a user's face aligned with the confining passageway of said hood section.

36. A steam generating and control section of a vaporizing device for generating steam which subsequently is to be directed to a region of a user's face, characterized in that said steam generating and control section includes a lower body section upstream of an upper body section, said upper body section having a peripheral sidewall defining an interior passage and an upper marginal edge defining a opening through which steam is permitted to exit from said steam generating and control section; a cup member for receiving a liquid to be vaporized and a heater means for heating said liquid being retained in said lower body section; and an adjustable valve assembly downstream of the cup member and upstream of the marginal edge of the upper body section for regulating the volume and velocity of steam flow exiting through said upper margin of said steam generating and control section, said adjustable valve assembly providing an open passageway for the downstream flow of steam in all adjustable settings of said assembly.

37. The steam generating and control section of claim 36 characterized in that said adjustable valve assembly includes a movable valve member, said valve member having an actuating lever means extending outwardly through a wall of the steam generating and control section for manual engagement by a user for adjusting the setting of said assembly.

38. The steam generating and control section of claim 36 further characterized by an air-inlet slot downstream of said cup member for permitting ambient air to enter the steam generating and control section and mix with steam moving in a downstream direction past said air-inlet slot.

39. The steam generating and control section of claim 38 further characterized by an exit slot for a portion of the steam and air mixfure, spaced downstream from the air-inlet slot, said exit slot being adjacent to an upstream end of said adjustable valve assembly and circumferentially offset from the air inlet slot.

* * * * *